United States Patent [19]

Shono et al.

[11] Patent Number: 5,130,136

[45] Date of Patent: Jul. 14, 1992

[54] MONOTERPENEDIOL INSECT REPELLENTS

[75] Inventors: Yoshinori Shono, Ibaraki; Keisuke Watanabe, Ashiya; Hiroko Sekihachi, Toyonaka; Akiko Kakimizu, Nishinomiya; Masaya Suzuki, Takarazuka; Noritada Matsuo, Itami, all of Japan

[73] Assignee: Sumitomo Chemical Company, Limited, Osaka, Japan

[21] Appl. No.: 745,359

[22] Filed: Aug. 15, 1991

[30] Foreign Application Priority Data

Sep. 18, 1990 [JP] Japan .................................. 2-249420
Mar. 25, 1991 [JP] Japan .................................. 3-086080
Aug. 9, 1991 [JP] Japan .................................. 3-224648

[51] Int. Cl.$^5$ ............................................. A01N 31/06
[52] U.S. Cl. ............................ 424/405; 424/DIG. 10; 424/403; 514/738; 514/919
[58] Field of Search ............... 424/403, DIG. 10, 405; 514/919, 738, 729

[56] References Cited

U.S. PATENT DOCUMENTS 2,407,205  9/1946  Wilkes .................................. 514/738
5,017,377  5/1991  Sikinami et al. ..................... 424/409

OTHER PUBLICATIONS

Synthetic Communcations, vol. 19 (11 & 12), 1939–1943 (1989), "One-Pot Two-Steps Synthesis of 1,2-Diol", F. Fringuelli et al.
Izv. Akad. Nauk, USSR Ser. Kim., 1983, vol. 10, 2391–2392, Kazakova et al., "Alkali-catalyzed hydration of stereoisomeric 3,4–epoxycaranes".
Aust. J. Chem. 1974, vol. 27, 2199–2204, Hamon et al., "The Determination of the Absolute Configuration of Vicinal Diols".
J. Org. Chem., vol. 42, No. 12, 1977, 2073–2076, Lund et al., "Asymmetric Reduction of Acetophenone with Lithium Aluminum Hydride Complexes of Terpenic Glycols".
J. Org. Chem., vol. 23, 1958, 1274–1276, Newhall, "Derivatives of (+)-Limonene. I. Esters of trans-p-Menthane-1,2-diol".
Abstracts of 6th International Conference of Agrochemical Society, 1986, 2D/E-07, Nishimura et al., "New Repellants Against Mosquitos, p-Menthane-3,-8-diols in Eucalyptus Citriodora and Related Compounds".
J. Amer. Chem. Soc., vol. 88, 1966, 4926–4934, Kropp, "Cyclopropyl Participation in the Carane System".

Primary Examiner—Thurman K. Page
Assistant Examiner—Neil Levy
Attorney, Agent, or Firm—Stevens, Davis, Miller & Mosher

[57] ABSTRACT

An insect repellent comprising as an active ingredient a monoterpenediol compound having the formula,

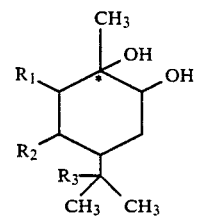

wherein $R_1$, $R_2$ and $R_3$ have either one of the following definitions:
(i) all of $R_1$, $R_2$ and $R_3$ are hydrogen,
(ii) $R_1$ is hydrogen and $R_2$ and $R_3$, taken together, form a carbon-carbon single bond, or
(iii) $R_2$ is hydrogen, $R_1$ and $R_3$, taken together, form a carbon-carbon single bond, and the hydroxyl bonded to the carbon atom marked with an asterisk takes an α-configuration.

16 Claims, No Drawings

MONOTERPENEDIOL INSECT REPELLENTS

The present invention relates to an insect repellent containing a monoterpenediol compound as an active ingredient.

Hitherto, as a repellent against blood-sucking insect pests such as mosquitoes, including Culex spp., Aedes spp. and Anopheles spp., black flies, stable flies, etc., N,N-diethyl-m-toluamide (hereinafter referred to as Deet) has been used in preparation forms such as sprays, lotions, creams, etc.

However, Deet has many disadvantages: The species of insect pests against which Deet is efficacious are limited, Deet is inferior in the efficacy against Anopheles spp. which are a vector of malaria, and Deet has an offensive odor and is soluble in resins.

In view of such a situation, the present inventors have extensively studied to develop an insect repellent in which these disadvantages have been overcome. As a result, the present inventors have found that a monoterpenediol compound having the following formula (I) (hereinafter referred to as present compound) exhibits a very high insect repellent effect,

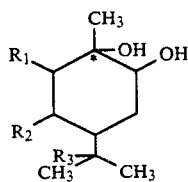

wherein $R_1$, $R_2$ and $R_3$ have either one of the following definitions:
(i) all of $R_1$, $R_2$ and $R_3$ are hydrogen,
(ii) $R_1$ is hydrogen and $R_2$ and $R_3$, taken together, form a carbon-carbon single bond, or
(iii) $R_2$ is hydrogen, $R_1$ and $R_3$, taken together, form a carbon-carbon single bond, and the hydroxyl bonded to the carbon atom marked with an asterisk takes an α-configuration referred to in the stereochemistry.

The present inventors thus completed the present invention.

The present compounds are known compounds described in the literatures. The literatures are specified as below.
  (i) A synthetic method for the p-menthanediol compound in which all of $R_1$, $R_2$ and $r_3$ are hydrogen is described in J. Org. Chem., Vol. 23, pp. 1274–1276 (1958); ibid., Vol. 42, pp. 2033–2037 (1977); etc.
  (ii) A synthetic method for caranediol in which $R_1$ is hydrogen and $R_2$ and $R_3$, taken together, form a carbon-carbon single bond is described in J. Amer. Chem. Soc., Vol. 88, pp. 4926–4934 (1966); Izv. Akad. Nauk USSR, Ser. Khim., Vol. 10, pp. 2391–2392 (1983); Synthetic Communication, Vol. 19, pp. 1939–1943 (1989); etc.
  (iii) A synthetic method for pinanediol, in which $R_2$ is hydrogen, $R_1$ and $R_2$, taken together, form a carbon-carbon single bond, and the hydroxyl bonded to the carbon atom marked with an asterisk takes an α-configuration, is described in Australian J. Chemistry, Vol. 127, pp. 2199–2204 (1974); etc.

The above p-menthanediol compound, caranediol and pinanediol have a stereoisomer. All these stereoisomers and their mixtures can be used as the active ingredient of the present insect repellent.

In the present compound represented by the formula (I), preferred compounds are those in which $R_1$, $R_2$, $R_3$ have either one of the following definitions:
  (i) all of $R_1$, $R_2$ and $R_3$ are hydrogen, and
  (ii) $R_1$ is hydrogen and $R_2$ and $R_3$, taken together, form a carbon-carbon single bond; and more preferred ones include:
    1R,2R,4R-p-menthane-1,2-diol,
    1R,2R,4S-p-menthane-1,2-diol,
    1S,3S,4R,6R-carane-3,4-diol,
    1S,3R,4R,6R-carane-3,4-diol and
    1S,3S,4S,6R-carane-3,4-diol, etc.

Some of the specific examples of the present compound are shown in Table 1.

TABLE 1

| Compound No. | Structural formula | Name of compound |
|---|---|---|
| (1) | [structure] | 1S,2R,4R-p-menthane-1,2-diol |
| (2) | [structure] | 1R,2R,4R-p-menthane-1,2-diol |
| (3) | [structure] | 1S,2S,4R-p-menthane-1,2-diol |
| (4) | [structure] | 1R,2S,4R-p-menthane-1,2-diol |
| (5) | [structure] | 1S,2R,4S-p-menthane-1,2-diol |
| (6) | [structure] | 1R,2R,4S-p-menthane-1,2-diol |

TABLE 1-continued

| Compound No. | Structural formula | Name of compound |
|---|---|---|
| (7) | | 1S,2S,4S-p-menthane-1,2-diol |
| (8) | | 1R,2S,4S-p-menthane-1,2-diol |
| (9) | | 1S,3S,4R,6R-carane-3,4-diol |
| (10) | | 1S,3R,4R,6R-carane-3,4-diol |
| (11) | | 1S,3S,4S,6R-carane-3,4-diol |
| (12) | | 1S,3R,4S,6R-carane-3,4-diol |
| (13) | | 1R,2R,3S,5R-pinane-2,3-diol |
| (14) | | 1R,2R,3R,5R-pinane-2,3-diol |
| (15) | | 1S,2S,3R,5S-pinane-2,3-diol |
| (16) | | 1S,2S,3S,5S-pinane-2,3-diol |

The insect pests against which the present compound is efficacious are blood-sucking pests, hygienic pests, etc. Specific examples of the blood-sucking pests are mosquitoes such as Anopheles spp. (e.g. *Anopheles albimanus*) which are a vector of malaria in the tropical zone, Aedes spp. (e.g. *Aedes aegypti, Aedes albopictus*), Culex spp. [e.g. common mosquito (*Culex pipiens pallens*), Culex tritaeniorhynchus], black flies, stable flies, sand flies, Culicoides spp., etc. Specific examples of the hygienic pests are housefly (*Musca domestica*), etc.

Some of the present compounds themselves can be used as an insect repellent. Usually, however, the present compounds are used in the form of a composition obtained by mixing with a suitable carrier (hereinafter referred to as present composition). The composition includes for example liquid formulations (e.g. lotions and aerosols) and cream formulations.

Specific examples of the carriers used in preparing the liquid formulations are water, alcohols (e.g. methanol, ethanol, cetyl alcohol, glycerin and polyethylene glycol), ethers (e.g. tetrahydrofuran and dioxane), aliphatic hydrocarbons (e.g. hexane, kerosene, paraffin and petroleum benzine) and esters (e.g. ethyl acetate).

Into the liquid formulations may be incorporated common auxiliaries for formulation such as emulsifiers or dispersing agents, spreading,wetting agents, suspending agents, preservatives, propellants, etc. Further, common film-forming agents may also be incorporated into the liquid formulations.

Specific examples of the auxiliaries are soaps, emulsifiers such as polyoxyethylene fatty acid alcohol ethers (e.g. polyoxyethylene oleyl ether), polyoxyethylene alkylaryl ethers (e.g. polyoxyethylene nonylphenyl ether), polyoxyethylene fatty acid esters, fatty acid glycerides, sorbitan fatty acid esters (e.g. polyoxyethylene sorbitan monostearate), sulfuric acid esters of a higher alcohol and sodium dodecylbenzenesulfonate; spreading.wetting agents such as glycerin and polyethylene glycol; suspending agents such as casein, gelatin, alginic acid, carboxymethyl cellulose, gum arabic, hydroxypropyl cellulose and bentonite; preservatives such as salicylic acid, methyl p-hydroxybenzoate, ethyl p-hydroxybenzoate, propyl p-hydroxybenzoate and butyl p-hydroxybenzoate; propellants such as dimethyl ether, chlorofluorocarbon and carbon dioxide gas; and various film-forming agents such as cellulose derivatives (e.g. nitrocellulose, acetylcellulose, acetylbutyrylcellulose and methyl cellulose), vinyl resins (e.g. vinyl acetate resins) and polyvinyl alcohol.

Specific examples of the carriers used in preparing cream formulations are hydrocarbons such as liquid paraffin, vaseline and paraffin; silicones such as dimethylsiloxane, colloidal silica and bentonite; alcohols such as ethanol, stearyl alcohol and lauryl alcohol; polyhydric alcohols such as polyethylene glycol, ethylene glycol and glycerin, carboxylic acids such as lauric acid and stearic acid; and esters such as beeswax and lanolin.

Into the cream formulations may be incorporated the same auxiliaries for formulation as incorporated into the liquid formulations. Further, the present compound may be used after microencapsulated and then formulated into lotions, aerosols, etc.

Into the present compositions may be incorporated other insect repellents, antioxidants, other additives, etc. Specific examples of the other incorporatable insect repellents are Deet, dimethyl phthalate, 2-ethyl-1,3-hexanediol, N-octylbicycloheptane dicarboximide, p-menthane-3,8-diol, 2,3,4,5-bis($\Delta^2$-butylene)tetrahydrofurfural, di-n-propyl isocinchomeronate, di-n-butyl succinate, 2-hydroxyethyl octyl sulfide and empenthrin [1-ethynyl-2-methyl-2-pentenyl d-cis,trans-chrysanthemate (cis:trans=2:8)]. Specific examples of the antioxidants are butylhydroxyanisole, dibutylhydroxytoluene, tocopherol and γ-oryzanol.

The present compositions formulated as described above or the present compounds themselves can be applied directly to skin, etc. Alternatively, they can be used by a method comprising applying them to a suitable sheet-form, film-form, net-form or band-form base material by treatment such as coating, impregnation, kneading, dropping, etc., and putting the repellent-applied base material directly onto exposed area of the skin or onto the clothing.

Specific examples of the constituents of the base materials are synthetic resins such as polyethylene, polypropylene, polyvinylidene chloride, polyester, vinylon and nylon; synthetic fibers made of these resins; animal and vegetable fibers such as silk, cotton and wool; inorganic fibers such as those made of aluminum; and the mixtures thereof. When a net-form base material is used, that of a finer mesh is more preferable. Generally, however, a size of about 16 or finer mesh is sufficiently effective.

The content of the present compound, an active ingredient, in the present composition varies with the preparation form and method of application. However, when the present compound is used in the form of liquid formulations (e.g. lotions and aerosols) or cream formulations, or it is used applied to the base material, its content is usually 0.1 to 70% by weight, preferably 1 to 40% by weight.

When the present composition is applied to the skin, the amount of the present compound is usually 0.01 to 2 mg, preferably 0.05 to 1 mg per 1 $cm^2$ of the area of the skin. This amount is also the same when the present compound alone is used.

The amount described above varies with the type of formulations, kind and gathering density of insect pests to be repelled, time at which the present composition is applied, weathering conditions, age of persons who use the present composition, and the like. Consequently, the amount can be increased or decreased irrespective of the above range.

The present invention will be illustrated more specifically with reference to the following Referential Examples, Formulation Examples and Test Examples. These examples, however, are not of course to be interpreted as limiting the present invention thereto

REFERENTIAL EXAMPLE 1

Production of 1S,2R,4R-p-menthane-1,2-diol [Compound (1)]

2.54 Grams of potassium permanganate and 0.55 g of sodium hydroxide were dissolved in 45 ml of water in a 100-ml flask and cooled to 0° C. To the resulting solution were added 1.5 g of 1S,2R,4R-D-1-menthene, 10 ml of tertbutyl alcohol, 25 g of ice and 10 ml of water. After stirring for 10 minutes, the mixed solution was allowed to stand for 12 hours to complete the reaction. The reaction solution was filtered to remove the insoluble matters. The organic layer, a filtrate, was extracted with three 60-ml portions of ethyl acetate. The ethyl acetate layer was dried over anhydrous magnesium sulfate. The solvent, ethyl acetate, was distilled off to obtain 1.5 g of a crude product. The crude product was subjected to column chromatography on silica gel using a hexane/ethyl acetate (1:1) mixed solvent to obtain 1.1 g of Compound (1) having a melting point of 77° to 78° C.

REFERENTIAL EXAMPLE 2

Production of 1R,2R,4R-p-menthane-1,2-diol [Compound (2)]and 1R,2R,4S-p-menthane-1,2-diol [Compound (6)]

To a 100-ml eggplant-form flask were added 10 g of limonene oxide and 50 ml of a 1% aqueous sulfuric acid solution. The mixture was stirred violently. To the mixture was added 50 ml of ethyl acetate. The ethyl acetate layer was dried over anhydrous magnesium sulfate Then, the dried ethyl acetate layer was concentrated to obtain 8 g of a reaction product. The reaction product was dissolved in 50 ml of ethyl acetate and hydrogenated with addition of 100 mg of a 5% palladium/carbon (Pd-C). The solution containing the hydrogenated reaction product was filtered to remove 5% Pd-C, dried over anhydrous magnesium sulfate and concentrated to obtain 7.8 g of a crude product. The crude Product was subjected to column chromatography on silica gel using a hexane/ethyl acetate (1:1) mixed solvent to obtain 3.5 g of Compound (2) having a melting point of 85° to 87° C. and 3.3 g of Compound (6) having a melting point of 64° to 65° C., separately.

REFERENTIAL EXAMPLE 3

Production of 1S,3S,4R,6R-carane-3,4-diol [Compound (9)]

To a 1,000-ml eggplant-form flask were added 20.45 g of 3-carene, 350 ml of tert-butyl alcohol and 150 ml of water. The mixture was cooled to 0° C. with stirring. To the mixture was added by drops a solution of 35.1 g of potassium permanganate and 7.5 g of sodium hydroxide in 600 ml of water over about 1 hour with stirring the mixture and with maintaining the reaction temperature at 10° C. or less. Stirring was continued at room temperature for 3 hours to complete the reaction. Therefore, the reaction solution was filtered to remove the insoluble matters. The filtrate was concentrated to 150 ml. Thereto were added 200 ml of a saturated aqueous sodium chloride solution and 500 ml of ethyl acetate. The organic layer was extracted with ethyl acetate. The ethyl acetate layer was dried over anhydrous magnesium sulfate. The solvent, ethyl acetate, was distilled off to obtain 17.0 g of a crude product. The crude product was subjected to column chromatography on silica gel using a hexane/ethyl acetate (1:1) mixed solvent to obtain 15.5 g of Compound (9) having a melting point of 69° C.

REFERENTIAL EXAMPLE 4

Production of 1S,3R,4R,6R-carane-3,4-diol [Compound (10)]

To a 100-ml eggplant-form flask were added 0.41 g ($3 \times 10^{-3}$ mole) of 3-carene and 20 ml of distilled water. The mixture was cooled to 0° C. with violent stirring. To the mixture was added 0.57 g ($3.3 \times 10^{-3}$ mole) of m-chloroperbenzoic acid over 5 to 10 minutes. Thereafter, the resulting mixture was stirred at 20° C. for 3 hours. Thereafter, 0.5 ml of 10% $H_2SO_4$ was added to the reaction solution. After stirring for 3 hours, sodium hydroxide was added to the solution until the solution became transparent. After adding sodium chloride to the transparent solution, the organic layer was extracted with three 20-ml portions of ethyl acetate. The ethyl acetate layer was dried over anhydrous magnesium sulfate and concentrated to obtain 0.40 g of a crude diol as an extract. The crude diol was recrystallized from ethyl acetate to obtain 0.35 g of Compound (10) having a melting point of 86° C.

REFERENTIAL EXAMPLE 5

Production of 1S,3S,4S,6R-carane-3,4-diol [Compound (11)]

To a 200-ml eggplant-form flask were added 9 g of 3-carene, 45 ml of methylene chloride and then 8.8 g of sodium hydrogencarbonate. The mixture was stirred violently. 18.2 Grams of m-chloroperbenzoic acid was added thereto over 10 to 20 minutes while cooling the mixture to 0° C. Thereafter, stirring was continued at 20° C. for 3 hours. After completion of the reaction, the reaction solution was filtered to remove the precipitates. The methylene chloride layer, a filtrate, was washed with 50 ml of a saturated aqueous sodium sulfite solution and then with 50 ml of a saturated aqueous sodium hydrogencarbonate solution. The washed methylene chloride layer was dried over 5 g of anhydrous sodium sulfate. The dried layer was concentrated to obtain 9.8 g of a crude product. The crude product was subjected to column chromatography on silica gel using hexane/ethyl acetate (20:1) mixed solvent to obtain 9.6 g of 3-carane epoxide.

9.6 Grams of 3-carane epoxide was added to 60 ml of a 2N aqueous potassium hydroxide solution. The resulting mixture wa put in a pressure-proof reactor and allowed to react for 48 hours under a condition of 170° C. $\times$ 5-7 kg/cm$^2$. After completion of the reaction, the organic layer was extracted with 100 ml of ethyl acetate, washed with water and dried over anhydrous magnesium sulfate. The organic layer was then filtered to remove magnesium sulfate and concentrated to obtain 8.7 g of a crude product. The crude product was subjected to column chromatography on silica gel using a hexane/ethyl acetate (3:1) mixed solvent to obtain 8.0 g of oily Compound (11).

REFERENTIAL EXAMPLE 6

Production of 1S,3R,4S,6R-carane-3,4-diol [Compound (12)]

To a 100-ml flask were added 2.4 g of Compound (10), 1.2 g of sodium acetate and 20 ml of methylene chloride. The mixture was cooled to 0° C. with violent stirring. To the mixture was added 3.6 g of pyridinium chlorochromate over 2 hours with ice-cooling. Thereafter, the resulting mixture was stirred at room temperature for 5 hours to complete the reaction. The reaction mixture was subjected to column chromatography with 20 g of Florisil (a trade name of commercially available magnesium silicate) as a stationary phase and eluted with 100 ml of methylene chloride to obtain 1.6 9 of a crude product. The crude product was subjected to column chromatography on silica gel using a hexane/ethyl acetate (4:1) mixed solvent to obtain 1.00 g of 3$\beta$-hydroxycarane-4-one.

0.16 Gram of lithium aluminum hydride was added to 5 ml of ether. The mixture was cooled to 0° C. with stirring under nitrogen gas flow. In the mixture was dissolved 1.0 g of 3$\beta$-hydroxycarane-4-one, and 3 ml of an ether solution was added dropwise thereto. The temperature of the mixed solution was returned to room temperature, and stirring was continued for 3 hours. After adding 1 ml of ethyl acetate to the stirred solution, the organic layer was washed with 5 ml of water, 5 ml of a 4N aqueous sodium hydroxide solution and 5 ml of a saturated aqueous sodium chloride solution in this order. The organic layer was dried over anhydrous magnesium sulfate and concentrated. The concentrate thus obtained was subjected to column chromatography on silica gel using a hexane/ethyl acetate (3:1) mixed solvent to obtain 0.4 g of Compound (12) as an oily product.

REFERENTIAL EXAMPLE 7

Production of 1R,2R,3S,5R-pinane-2,3-diol [Compound (13)]

To a 100-ml flask were added 1.17 g of potassium permanganate and 0.25 g of sodium hydroxide. The mixture was cooled to 0° C. To the cooled mixture were added 0.68 g of 1S-(−)-$\alpha$-pinene, 50 ml of tert-butyl alcohol, 25 g of ice and 10 ml of water. The resulting mixture was stirred for 10 minutes and then allowed to stand for a whole day and night to complete the reaction. The reaction solution was filtered to remove the insoluble matters. The organic layer, a filtrate, was extracted with three 160-ml portions of ethyl acetate. The ethyl acetate layer was dried over anhydrous magnesium sulfate. The solvent, ethyl acetate, was distilled off to obtain 0.4 g of a crude product. The crude product was subjected to thin-layer chromatography on silica gel using a hexane/ethyl acetate (1:1) mixed solvent to obtain 0.25 g of Compound (13).

REFERENTIAL EXAMPLE 8

Production of 1S,2S,3R,5S-pinane-2,3-diol [Compound (15)]

The same procedure as in Referential Example 7 was repeated except that 1R-(+)-$\alpha$-pinene was used in place of 1S-(−)-α-pinene, to obtain 0.26 g of Compound (15) having a melting point of 57° C.

Next, Formulation Examples will be shown. In the examples, all parts are by weight, and the present compound is shown by Compound No. in Table 1.

FORMULATION EXAMPLE 1

Ten parts each of Compounds (1) to (16) is dissolved in a small amount of ethanol, and the solution was diluted with ethanol so that the total weight is made up to 35 parts. Each solution thus obtained is charged into an aerosol container, and a valve part is attached to the container. Thereafter, 65 parts of a freon 11/freon 12 (1:1) mixture, a propellant, is compressed into the container under pressure through the valve part. Thus, an aerosol of each Compound is obtained.

FORMULATION EXAMPLE 2

Five parts of Compound (2) and 5 parts of Compound (6) are dissolved in a small amount of ethanol, and the solution was diluted with ethanol so that the total weight is made up to 35 parts. The solution thus obtained is charged into an aerosol container. An aerosol is obtained in the same manner as in Formulation Example 1.

FORMULATION EXAMPLE 3

To 10 parts of Compound (10) are added 10 parts of stearic acid, 2 parts of cetyl alcohol, 1 part of lanolin, 2 parts of liquid paraffin and 62 parts of water. The mixture is melted by heating and stirred to obtain a uniform solution. 13 Parts of hot glycerin is injected into the solution, which is then thoroughly stirred to obtain a cream formulation.

FORMULATION EXAMPLE 4

A mixture containing 6 parts of stearic acid, 0.5 part of lanolin and 6 parts of Tween 60 (a trade name of polyoxyethylene sorbitan monostearate) is heated to 80° C. and injected into a 60° C. mixture of 75 parts of water and 2.5 parts of salicylic acid. Immediately, 10 parts of Compound (11) is added thereto with rapid stirring to obtain a lotion.

Next, Test Examples will be shown in order to make it clear that the present compounds are useful as an active ingredient for insect repellents. The present compounds are shown by Compound No. in Table 1.

TEST EXAMPLE 1

A chick whose abdominal feathers had been removed with haircutter was fixed on a wood board (7×15 cm) and 2.5×4 cm of its abdominal skin was exposed. The ethanol solution of each of the test compounds or the mixture thereof (90 μl) was treated on this area. The concentration is 1500 mg/m². About five hundred adult mosquitoes which were 6 to 8 days old after emergence (Anooheles albimanus: approximately equal number of female and male) were released in a cage (21×21×30 cm) made of stainless steel and nylon gauze. The two chicks were put on the cage and the treated areas were contacted with the nylon gauze. After 1 minute, number of attracted mosquitoes on the treated area was counted. The same procedure on the same cage was done on the untreated chicks. Two cages were used in each observation. The observation was continued until the repellency (%) decreased. Repellency (%) was calculated according to the following equation.

$$\text{Repellency (\%)} = \left(1 - \frac{\text{No. of attracted mosquitoes at treated chicks}}{\text{No. of attracted mosquitos at untreated chicks}}\right) \times 100$$

Once the repellency (%) was reduced to 70% or less, the counting was terminated. Table 2 shows the result.

TABLE 2

| | Repellent effect on *Anopheles albimanus* | | |
|---|---|---|---|
| | Repellency (%) | | |
| Test compound | Immediately after treatment | After 1 hour | After 2 hours |
| (1) | 95 | 86 | 72 |
| (2) | 95 | 93 | 65 |
| 50:50 Mixture of (2) and (6) | 93 | 88 | 76 |
| (9) | 92 | 64 | — |
| (10) | 95 | 88 | 85 |
| (11) | 100 | 90 | 62 |
| (12) | 100 | 70 | — |
| (13) | 99 | 72 | 45 |
| Deet | 88 | 47 | — |

TEST EXAMPLE 2

A chick whose abdominal feathers had been removed with haircutter was fixed on a wood board (7×15 cm) and 2.5×4 cm of its abdominal skin was exposed. The ethanol solution of each of the test compounds or the mixture thereof (90 μ) was treated on this area. The concentration is 1500 mg/m². About five hundred adult mosquitoes which were 6 to 8 days old after emergence (Aedes aeovoti: approximately equal number of female and male) were released in a cage (21×21×30 cm) made of stainless steel and nylon gauze. The two chicks were put on the cage and the treated areas were contacted with the nylon gauze. After 2 minutes, number of attracted mosquitoes on the treated area was counted. The same procedure on the same cage was done on the untreated chicks. Two cages were used in each observation. The observation was continued until the repellency (%) decreased. Repellency (%) was calculated according to the following equation.

$$\text{Repellency (\%)} = \left(1 - \frac{\text{No. of attracted mosquitoes at treated chicks}}{\text{No. of attracted mosquitos at untreated chicks}}\right) \times 100$$

Once the repellency was reduced to 70% or less, the counting was terminated. Table 3 shows the result.

TABLE 3

| | Repellent effect on *Aedes aegypti* | | | |
|---|---|---|---|---|
| | Repellency (%) | | | |
| Test compound | Immediately after treatment | After 1 hour | After 2 hours | After 3 hours |
| (1) | 100 | 95 | 83 | 72 |
| (2) | 100 | 92 | 87 | 75 |
| (6) | 95 | 93 | 92 | 89 |
| 50:50 Mixture of (2) and (6) | 100 | 100 | 95 | 92 |
| (9) | 99 | 92 | 81 | 70 |
| (10) | 96 | 93 | 71 | 65 |
| (11) | 100 | 95 | 67 | — |
| (12) | 100 | 85 | 65 | — |

TABLE 3-continued

| | Repellent effect on *Aedes aegypti* | | | |
| | Repellency (%) | | | |
| Test compound | Immediately after treatment | After 1 hour | After 2 hours | After 3 hours |
| --- | --- | --- | --- | --- |
| (13) | 100 | 96 | 62 | — |
| (15) | 100 | 85 | 65 | — |
| Deet | 100 | 82 | 60 | — |

What is claimed is:

1. An insect repellent composition which comprises as an active ingredient an insect repellently effective amount of a monoterpenediol compound having the formula,

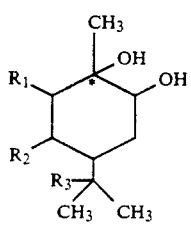

wherein $R_1$, $R_2$ and $R_3$ have one of the following definitions:

(i) all of $R_1$, $R_2$ and $R_3$ are hydrogen, (ii) $R_1$ is hydrogen and $R_2$ and $R_3$, taken together, form a carbon-carbon single bond, or (iii) $R_2$ is hydrogen, $R_1$ and $R_3$, taken together, form a carbon-carbon single bond, and the hydroxyl bonded to the carbon atom marked with an asterisk takes an α-configuration, and an inert carrier.

2. The insect repellent of claim 1, wherein the monoterpenediol compound is a compound in which all of $R_1$, $R_2$ and $R_3$ are hydrogen.

3. The insect repellent of claim 2, wherein the monoterpenediol compound is 1R,2R,4R-p-menthane-1,2-diol.

4. The insect repellent of claim 2, wherein the monoterpenediol compound is 1R,2R,4S-p-menthane-1,2-diol.

5. The insect repellent of claim 2, wherein the monoterpenediol compound is a mixture of 1R,2R,4R-p-menthane-1,2-diol.

6. The insect repellent of claim 1, wherein the monoterpenediol compound is a compound in which $R_1$ is hydrogen and $R_2$ and $R_3$, taken together, form a carbon-carbon single bond.

7. The insect repellent of claim 6, wherein the monoterpenediol compound is 1S,3S,4R,6R-carane-3,4-diol.

8. The insect repellent of claim 6, wherein the monoterpenediol compound is 1S,3R,4R,6R-carane-3,4-diol.

9. The insect repellent of claim 6, wherein the monoterpenediol compound is 1S,3S,4S,6R-carane-3,4-diol.

10. The insect repellent composition of claim 1, wherein the repellent is a liquid or cream formulation and the amount of the monoterpenediol compound present is 0.1 to 70% by weight.

11. A method according to claim 3, wherein the insect repellent composition comprises 0.1 to 70% by weight of the monoterpenediol compound applied to the base material.

12. A method for repelling insects which comprises: applying an insect repellent composition comprising as an active ingredient an insect repellently effective amount of at least one monoterpenediol compound having the formula,

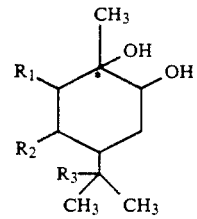

wherein $R_1$, $R_2$ and $R_3$ have one of the following definitions:

(i) all of $R_1$, $R_2$ and $R_3$ are hydrogen, (ii) $R_1$ is hydrogen and $R_2$ and $R_3$, taken together, form a carbon-carbon single bond, or (iii) $R_2$ is hydrogen, $R_1$ and $R_3$, taken together, form a carbon-carbon single bond, and the hydroxyl bonded to the carbon atom marked with an asterisk takes an α-configuration, and an inert carrier directly to skin.

13. A method for repelling insects which comprises:

(a) applying an insect repellent composition comprising as an active ingredient an insect repellently effective amount of at least one monoterpenediol compound having the formula,

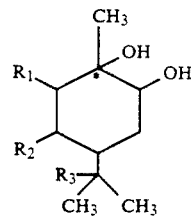

wherein $R_1$, $R_2$ and $R_3$ have one of the following definitions:

(i) all of $R_1$, $R_2$ and $R_3$ are hydrogen, (ii) $R_1$ is hydrogen and $R_2$ and $R_3$, taken together, form a carbon-carbon single bond, or (iii) $R_2$ is hydrogen, $R_1$ and $R_3$, taken together, form a carbon-carbon single bond, and the hydroxyl bonded to the carbon atom marked with an asterisk takes an α-configuration, and an inert carrier to a suitable base material, and (b) applying the repellent-applied base material directly onto skin or onto clothing.

14. The method according to claim 12, wherein the insects repelled are selected from the group consisting of blood-sucking pests and hygienic pests.

15. The method according to claim 13, wherein the insects repelled are selected from the group consisting of blood-sucking pests and hygienic pests.

16. A method according to claim 12, wherein the amount of the monoterpenediol compound applied to the skin is 0.01 to 2 mg per 1 $cm^2$ of area of the skin.

* * * * *

UNITED STATES PATENT AND TRADEMARK OFFICE
CERTIFICATE OF CORRECTION

PATENT NO. : 5,130,136
DATED : JULY 14, 1992
INVENTOR(S) : YOSHINORI SHONO ET AL.

It is certified that error appears in the above-indentified patent and that said Letters Patent is hereby corrected as shown below:

<u>Column 11</u>

Claim 11, line 1, change "3" to --13--.

Signed and Sealed this

Nineteenth Day of March, 1996

Attest:

BRUCE LEHMAN

Attesting Officer     *Commissioner of Patents and Trademarks*